United States Patent [19]

Heimke et al.

[11] 4,407,022

[45] Oct. 4, 1983

[54] FEMUR COMPONENT FOR AN ARTIFICIAL HIP JOINT

[75] Inventors: Gunther Heimke, Weinheim; Peter Griss, Plankstadt, both of Fed. Rep. of Germany

[73] Assignee: Steinzeug- und Kunststoffwerke Friedrichsfeld GmbH, Mannheim, Fed. Rep. of Germany

[21] Appl. No.: 274,208

[22] Filed: Jun. 16, 1981

Related U.S. Application Data

[63] Continuation of Ser. No. 63,681, Aug. 6, 1979, abandoned.

[30] Foreign Application Priority Data

Aug. 4, 1978 [DE] Fed. Rep. of Germany ....... 2834155

[51] Int. Cl.³ ............................................... A61F 1/03
[52] U.S. Cl. ................................ 3/1.913; 128/92 CA
[58] Field of Search ............. 128/92 C, 92 CA; 3/1.9, 3/1.91, 1.911, 1.912, 1.913

[56] References Cited

U.S. PATENT DOCUMENTS 4,031,571  6/1977  Heimke et al. ........................ 3/1.913

Primary Examiner—Clifford D. Crowder
Attorney, Agent, or Firm—Fisher, Christen & Sabol

[57] ABSTRACT

The shaft portion of an artificial hip joint intended for cement-free anchoring in a femur which is generally rectangular in cross-section and is provided with outwardly projecting steps for direct transfer of axial forces between the shaft and the bone tissue, one half of the steps being transversely inclined with respect to the shaft axis with the other half of the steps inclined in the opposite direction by an equal amount to prevent rotation of the shaft as a result of the development of equal and opposite components of force.

9 Claims, 2 Drawing Figures

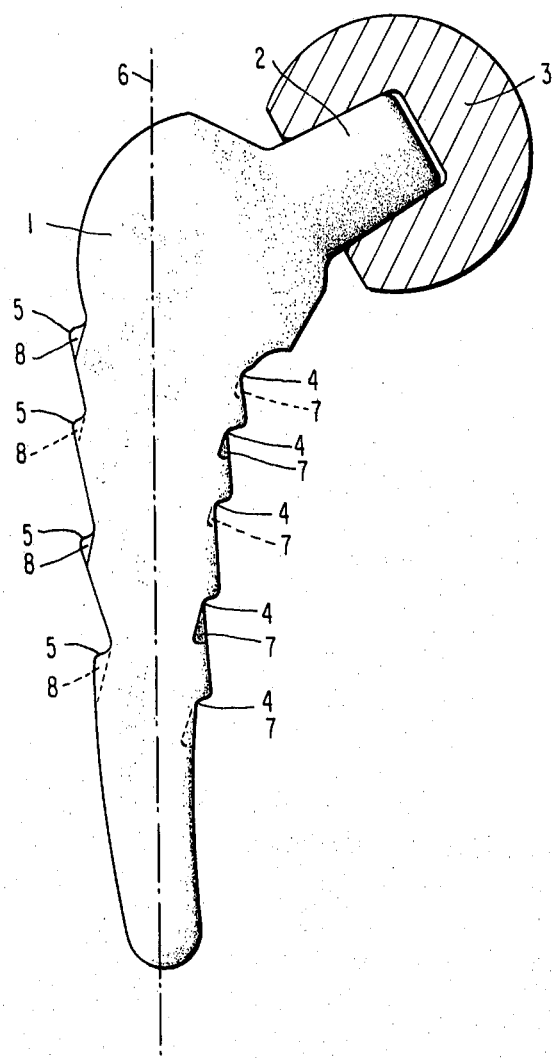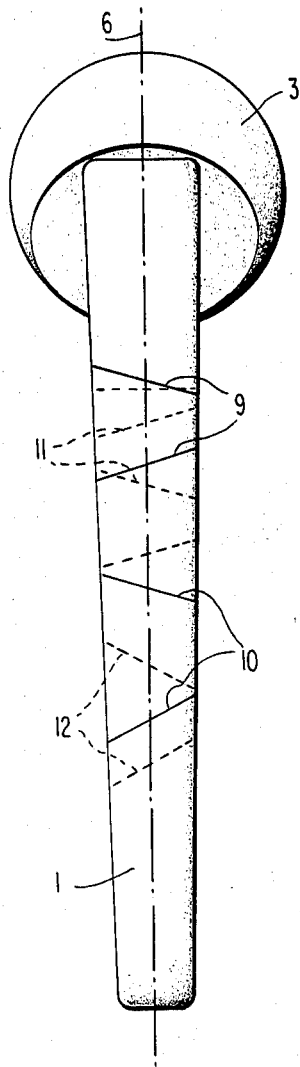

FEMUR COMPONENT FOR AN ARTIFICIAL HIP JOINT

This application is a continuation of our prior co-pending application Ser. No. 63,681, filed Aug. 6, 1979, now abandoned.

The invention concerns the femur component of a hip endoprosthesis for cement-free anchoring which has steps distributed on at least the medial and the lateral side over the length of its anchoring shaft.

Artificial hip joints are used to replace hip joints damaged by disease or accident. The femur component of such an endoprosthesis must substitute for the function of the femur head. The generally spherical parts which articulate with the corresponding component of the hip must be anchored in the femur. For this purpose, most femur components of artificial hip joints have shafts by means of which they are anchored in the narrow base of the femur. In addition, a plastic bone cement is used to anchor these shafts, which in the great majority of cases are manufactured from metals or metal alloys. Since these plastic bone cements have certain drawbacks, however, attempts are continually being made to devise anchoring shafts which permit a cement-free anchoring of the femur component.

To achieve this direct, i.e. cement-free anchoring of the femur component of hip endoprostheses, various forms of prostheses have been proposed. The materials envisioned for these prostheses are usually metals or metal alloys. The possibilities of achieving the goal of a secure cement-free anchoring were considerably improved after it became known that certain ceramics display better tolerability with respect to bony tissue than metal or plastics. This lead to a series of designs of femur components in which such bio-inert ceramic materials are provided either in compact form or as a dense ceramic coating on metal parts (British Specification No. 1,451,283 and U.S. Pat. No. 3,919,723). Within the framework of these developments, it became known that at least dense high purity $Al_2O_3$ ceramic permits the construction of strong bone structure on surfaces which carry the loads perpendicularly, i.e. exposed to pure compressive forces. This was summarily disclosed in Research Report T 77-70 of the Federal Ministry for Research and Technology of December, 1977. On the basis of these facts, a femur part of a total hip joint endoprosthesis for cement-free implantation was designed which was optimally adapted to the current state of the art (U.S. Pat. No. 4,031,571). The possibility of the reaction of the bony tissue on the medial side of the shaft of the prosthesis was taken into account in this case by including steps oriented in such a way that their pressure-transmitting surfaces were always perpendicular to the direction of orientation of the laminar bone structure at the site of the step in question. This was arranged on the medial side of the shaft for direct pressure transmission; on the lateral side, the steps were oriented in the opposite direction, since it was anticipated that the corresponding pressure-receiving bony structures would form there, from which the essentially tension-transmitting structures would pass the forces occurring there on to the lateral corticalis of the femur. The very extensive animal experimental studies have shown that the anticipated effect did indeed occur, but it was still not sufficient to stabilize the prosthesis in the bone space. In other words, in this way it was still not possible to stabilize the prosthesis against rotational movements about the axis of the femur. It was attempted to solve the problem of rotation stabilization of the prosthesis with respect to rotary movements about the femur axis by applying grooves with an asymmetrical cross section and running obliquely, on the remaining side surfaces of the prosthesis. The corresponding proposal is described in detail in U.S. Pat. No. 4,031,571. Extensive animal experimental studies in this case also showed, however, that rotational stability still cannot be achieved to an extent that would justify switching from animal experiments to clinical testing. The rotational stabilization of the prosthesis with respect to rotary movements about the femur axis also still could not be satisfactorily assured with this device in a sufficient number of cases.

Therefore, the problem still remains of finding a design which will assure a rotational stabilization of the prosthesis with respect to rotary movements about the femur axis.

This problem is solved by this invention by having the force-transmitting steps project outwardly from the medial and lateral sides of the shaft generally at right angles with respect to a first plane which passes through the shaft axis and which is generally normal to the planes of the front and rear surfaces of the shaft and also by having the steps disposed with varying inclinations with respect to a second plane which passes through the shaft axis and which is disposed generally parallel with the planes of the front and rear surfaces of the shaft.

This can be arranged in such a way that neighboring steps on either the medial or lateral side which have their force-transmitting surfaces disposed generally at right angles to said first plane may also be inclined respectively in angular directions with respect to said second plane having opposite directions. It is also possible for the inclinations of these steps to be in opposite directions but to have the same angular values with respect to said second plane. In other words, the inclinations of any two neighboring force-transmitting surfaces can have the same angular values with respect to said second plane but be inclined in opposite directions. According to the current state of the art, it is favorable if the inclinations of the steps have values smaller than 30° with respect to said second plane.

Initial orientative animal experiments with shafts manufactured according to the characteristics of this invention suggest that through the measures according to the invention, indeed a better rotational stabilization can be achieved. In particular, it has been found that the pressure-receiving bone structures in close contact with dense high-purity $Al_2O_3$ ceramic can also form on pressure-transmitting surfaces where the pressure or the pressure variations are not oriented exactly perpendicularly to the interface. Since all attempts at cement-free fixation of femur components of hip endoprostheses by means of a shaft in the narrow channel of the femur until now had failed to the extent that rotational stability about the shaft and femur axis could not be achieved, the arrangement of the steps according to the invention represents a decisive advance. This favorable finding is also in contrast with the results achieved with artificial joints according to U.S. Pat. No. 4,031,571. According to the present state of the art, it is apparent that the distances for the bone tissue to grow into the grooves on the side surfaces of the shaft, as stipulated in the U.S. Pat. No. 4,031,571 cited above, from the corticalis into these grooves, are too large. If these corresponding prosthesis surfaces are given a more strongly convex shape so that the distances become smaller, then the possibilities for the formation of blood vessels to supply the inner parts of the bone walls are significantly reduced. The present favorable results with the orientation of the pressure transmitting surfaces of the steps that have been proposed according to the present invention obviously permit the prosthesis to be stabilized against rotational movements about the femur axis while maintaining relatively wider intervening spaces on the two remaining prosthesis surfaces which favor the blood supply in the inner parts of the bone wall.

One variant of the invention is shown in the drawings, in which FIG. 1 is a front elevation and FIG. 2 is an elevational view from the lateral side.

FIG. 1 shows the femur component of a hip endoprosthesis with the shaft 1 to be anchored in the narrow space of the femur. This shaft carries a pin 2 at its upper end with which the connection with the replacement ball 3 of the hip head is formed. Designs are also possible and well known in which the hip joint replacement and the shaft are manufactured as a single unit. The shaft has different steps 4 on its medial side which are oriented in such a way that the pressure transmitting surfaces in this side view are as close as possible to perpendicular to the pressure-accepting bony structure in the areas in question. On the lateral side, the corresponding steps 5 are provided, which, however, are oriented upwardly with their pressure-transmitting surfaces. As stated in U.S. Pat. No. 4,031,571, they serve to achieve a stabilization of the prosthesis with respect to tilting movements in the medial direction. These steps 4 and 5 are inclined with respect to the plane of FIG. 1. This is brought to expression in the view of FIG. 1 by the outline marked 7 and 8. In the representation of FIG. 2, this becomes clearer. It represents a lateral view of the prosthesis. Here again, the shaft of the prosthesis is designated 1, the head of the prosthesis 3. Again, the axis of the prosthesis is designated 6. According to the invention, the deviation of the pressure-transmitting surfaces on the lateral side with respect to their orientation with respect to the shaft axis is clearly evident. Thus, the two upper steps designated generally by numeral 9 in FIG. 2 deviate by a total of 15° from the orientation perpendicular to the shaft axis. The two lower steps on the lateral side, designated generally by numeral 10, display a greater deviation, e.g. 30°. The inclination of the steps designated generally by numerals 11 and 12 on the medial side of the shaft is indicated by a broken line.

All bio-inert materials come into question as materials for these shafts. The results to date were achieved with shafts of dense high-purity $Al_2O_3$ ceramic. In this case, the femur components according to the invention were manufactured in one piece. However, it is also possible to make the shaft 1 of a metal alloy that can be tolerated by the body, e.g. titanium. It is also possible to make these shafts of metal and to coat their surface with a glass ceramic or enamel that can be tolerated by the body, as described in British specification No. 1,451,283.

For the implantation of these prostheses in animal experiments, the femurs were prepared with a file in accordance with the contour of the enveloping ends of the shaft of the prosthesis. The results thus far show that the restructuring of the bony tissue along the pressure-transmitting surfaces formed according to the invention leads to an improvement in the rotational stabilization of the prosthesis. The precise preparation of the bone bed of the pressure-transmitting steps oriented in accordance with the invention can, however, produce additional improvements, above all with respect to the rate at which the restructuring process occurred in the interfaces of the bony tissue.

We claim:

1. An artifical hip joint having an elongated shaft to be anchored in a femur without the use of cement, the cross-sectional outline of said shaft being generally rectangular, two of the oppositely disposed sides of said shaft being each provided with at least two outwardly projecting force-transmitting steps, the remaining two opposite sides of the shaft being smooth, each of the two steps on each of the opposite sides of the shaft being transversely inclined with respect to a plane which passes through the axis of the shaft and which is generally parallel with the planes of the smooth sides of the shaft in equal and opposite directions with respect to each other and said plane to transmit components of compression forces to the tissue of the femur to prevent rotation of the shaft about its long axis, and also in the direction of the shaft axis.

2. An artificial hip joint as defined in claim 1, wherein adjacent steps on the same side of the shaft are provided with opposite transverse inclinations.

3. An artificial hip joint as defined in either claim 1 or 2, wherein the angle of inclination of each step is less than 30°.

4. An artificial hip joint as defined in claim 3, wherein the angle of inclination of each step is at least 15°.

5. An artificial hip joint as defined in claim 4, wherein the steps are provided only on the medial and lateral sides of the shaft.

6. An artificial hip joint as defined in claim 1, wherein the angle of transverse inclination of two adjacent steps on one side of the shaft are of equal magnitude and of opposite direction.

7. An artificial hip joint as defined in claim 6, wherein the angle of inclination of each step is less than 30°.

8. An artificial hip joint as defined in claim 7, wherein the angle of inclination of each step is at least 15°.

9. An artificial hip joint as defined in claim 8, wherein the steps are provided only on the medial and lateral sides of the shaft.

* * * * *

UNITED STATES PATENT OFFICE
CERTIFICATE OF CORRECTION

Patent No. 4,407,022              Dated October 4, 1983

Inventor(s) Gunther Heimke and Peter Griss

It is certified that error appears in the above-identified patent and that said Letters Patent are hereby corrected as shown below:

On the title page, Item [73] should read:

-- [73] Assignee: Friedrichsfeld GmbH Steinzeug- und Kunststoffwerke. --

*Signed and Sealed this*

*Twenty-seventh* Day of *December 1983*

[SEAL]

*Attest:*

*Attesting Officer*

GERALD J. MOSSINGHOFF

*Commissioner of Patents and Trademarks*